United States Patent
Bodhuri et al.

(10) Patent No.: US 10,513,504 B2
(45) Date of Patent: Dec. 24, 2019

(54) PROCESSES FOR THE PREPARATION OF APALUTAMIDE AND INTERMEDIATES THEREOF

(71) Applicant: Apotex Inc., Toronto (CA)

(72) Inventors: Prabhudas Bodhuri, Torrance, CA (US); Alfredo Paul Ceccarelli, Brantford (CA); Michael R. Emmett, London (CA); Avedis Karadeolian, Cambridge (CA); Fabio E. S. Souza, Mississauga (CA); Gamini Weeratunga, Ancaster (CA); Boris Gorin, Oakville (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 16/294,259

(22) Filed: Mar. 6, 2019

(65) Prior Publication Data

US 2019/0276424 A1 Sep. 12, 2019

Related U.S. Application Data

(60) Provisional application No. 62/640,214, filed on Mar. 8, 2018.

(51) Int. Cl.
| | |
|---|---|
| *C07D 401/04* | (2006.01) |
| *C07C 231/12* | (2006.01) |
| *C07D 249/04* | (2006.01) |
| *C07D 207/40* | (2006.01) |
| *C07D 233/56* | (2006.01) |
| *C07C 237/30* | (2006.01) |

(52) U.S. Cl.
CPC .......... *C07D 401/04* (2013.01); *C07C 231/12* (2013.01); *C07C 237/30* (2013.01); *C07D 207/40* (2013.01); *C07D 233/56* (2013.01); *C07D 249/04* (2013.01)

(58) Field of Classification Search
CPC .................................................. C07D 401/04
USPC .......................................................... 546/15
See application file for complete search history.

(56) References Cited

U.S. PATENT DOCUMENTS

| | | |
|---|---|---|
| 2016/0152592 A1 | 6/2016 | Chen et al. |
| 2018/0201601 A1 | 7/2018 | Chen et al. |

FOREIGN PATENT DOCUMENTS

| | | |
|---|---|---|
| CN | 107501237 A | 12/2017 |
| CN | 108047200 A | 5/2018 |
| CN | 108069869 A | 5/2018 |
| CN | 108383749 A | 8/2018 |
| WO | 2005019158 A1 | 3/2005 |
| WO | 2006021759 A1 | 3/2006 |
| WO | 2006124118 A1 | 11/2006 |
| WO | 2007126765 A2 | 11/2007 |
| WO | 2008119015 A2 | 10/2008 |
| WO | 2011103202 A2 | 8/2011 |
| WO | 2012073138 A1 | 6/2012 |
| WO | 2016100645 A1 | 6/2016 |
| WO | 2016100652 A2 | 6/2016 |
| WO | 2017123542 A1 | 7/2017 |
| WO | 2018112001 A1 | 6/2018 |
| WO | 2018136001 A1 | 7/2018 |

OTHER PUBLICATIONS

Chodnekar et al., "Synthesis and Muscle-Relaxing Activity of o-, m-, and p-Alkylsulfonylbenzamides and Related Isoquinoline Derivates", Journal of Medicinal Chemistry Sep. 1968, p. 1023-1028.
Estieu et al., "A New Cyclobutane Ring Contraction: the Base-Induced Rearrangement of an a-Bromocyclobutanexarboxylic Ester", Tetrahedon Letters, 1996, p. 623-624, vol. 37, No. 5.
Xu et al., "A convenient synthesis of 4-amino-2-fluoro-N-methyl-benzamide", Journal of Chemical Research, Oct. 2013, p. 615-616.

*Primary Examiner* — Patricia L Morris
(74) *Attorney, Agent, or Firm* — The Webb Law Firm

(57) ABSTRACT

The present invention provides processes for the preparation of Apalutamide (1), as well as intermediates useful in the preparation thereof. In particular, the process of the invention utilizes the intermediate compound of Formula (2), wherein G is OH or a leaving group, which provides improvements over the known processes for the preparation of Apalutamide (1).

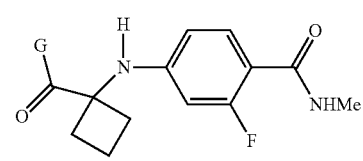

19 Claims, No Drawings

PROCESSES FOR THE PREPARATION OF APALUTAMIDE AND INTERMEDIATES THEREOF

CROSS-REFERENCE TO RELATED APPLICATION

This application claims the benefit of U.S. Provisional Patent Application No. 62/640,214, filed Mar. 8, 2018, the disclosure of which is hereby incorporated by reference in its entirety.

BACKGROUND OF THE INVENTION

Field of the Invention

The present invention relates to processes for the preparation of Apalutamide and intermediates used in the preparation thereof.

Description of Related Art

Apalutamide, or 4-[7-[6-cyano-5-(trifluoromethyl)pyridin-3-yl]-8-oxo-6-sulfanylidene-5,7-diazaspiro[3.4]octan-5-yl]-2-fluoro-N-methylbenzamide, exhibits activity as a nonsteroidal antiandrogen (NSAA), and is marketed in the United States as ERLEADA™, indicated for the treatment of patients with non-metastatic castration-resistant prostate cancer. Apalutamide (1) has the following structural formula:

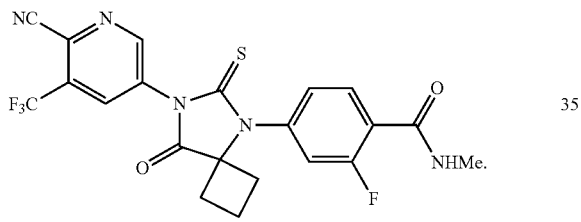

One method of preparing Apalutamide (1) is described in WO 2007/126765 A2, which discloses a family of compounds that are stated to be useful in the prevention or treatment of hyperproliferative diseases or disorders. In this method, which is depicted in Scheme 1, Apalutamide (1) is prepared by microwave-induced reaction of isothiocyanate (B) with nitrile (D), which are prepared, respectively, from pyridine (A) by treatment with thiophosgene, and by reaction of aniline (C) with cyclobutanone in the presence of sodium cyanide.

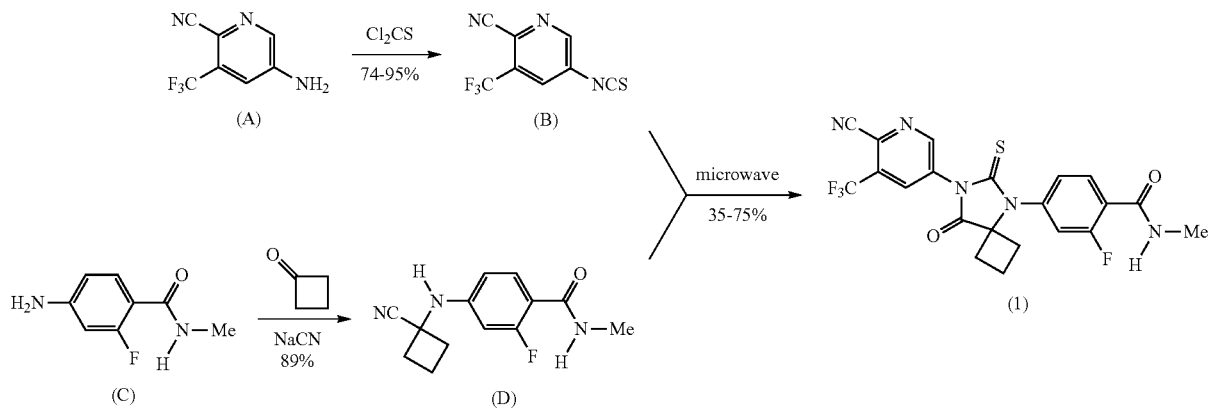

Scheme 1 (Prior Art)

A similar method is reported in WO 2008/119015 A2, which involves formation of the isothiocyanate (B) in situ from (A), but which avoids the use of microwave radiation in the final reaction step. In WO 2016/100645 A1, Apalutamide (1) is prepared by conversion of a final intermediate bearing an iodide substituent in place of the required N-methylamide group, wherein the iodide intermediate is prepared in an analogous manner to that described for preparation of Apalutamide (1) in WO 2008/119015 A2.

A central problem with these methods to prepare Apalutamide (1) is the requirement for sodium cyanide, a highly toxic and hazardous substance requiring specialised transport, handling and disposal practices. This leads to undue complexity and cost in the manufacture of Apalutamide (1) in a commercial setting.

A second process for the preparation of Apalutamide (1) is described in WO 2016/100652 A2. In this process, which is exemplified in Scheme 2, Apalutamide (1) is prepared from pyridine (A) by reaction with N-butoxycarbonyl (BOC)-protected cyclobutanecarboxylic acid (E), followed by deprotection of the resulting amide (F) to provide amine (G). N-arylation of amine (G) with aryl halide (H) and thiohydantoin ring formation yields Apalutamide (1), either directly when W is N-methylamide, or following amidation of the compound of Formula (J) when W is methoxy.

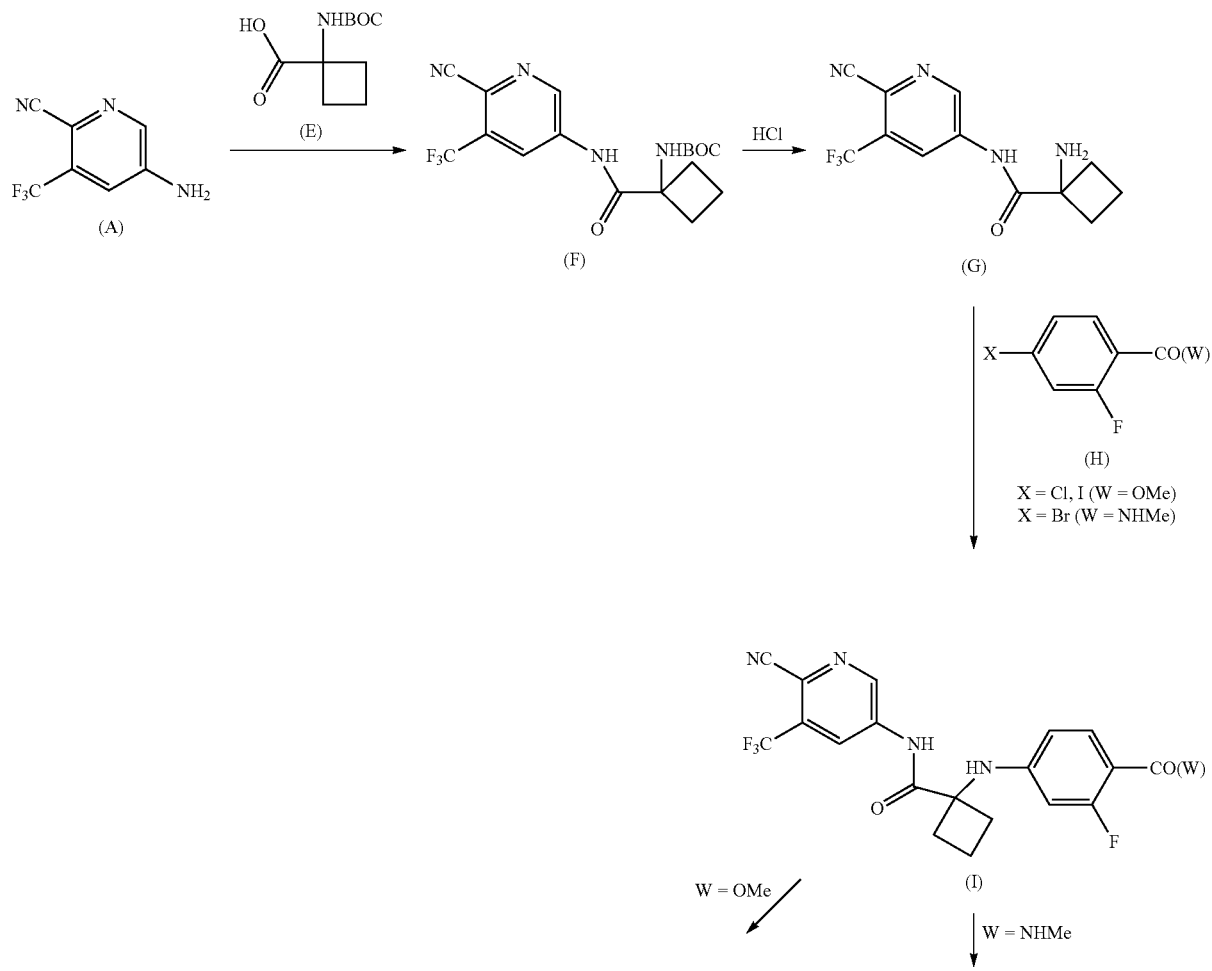

Scheme 2 (Prior Art)

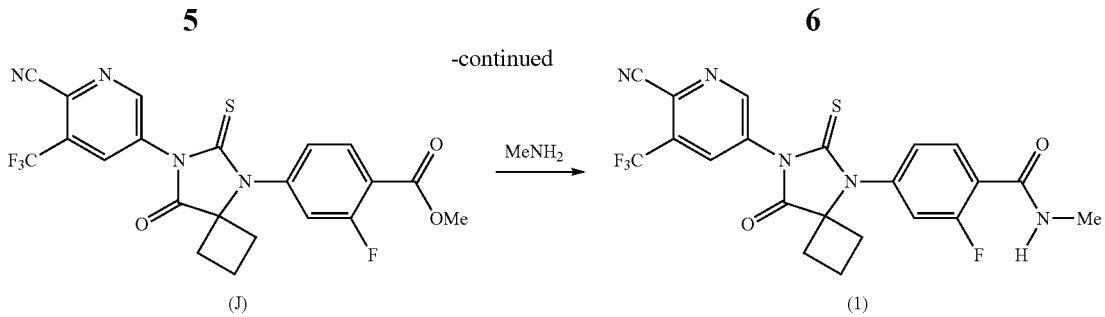

Although this approach avoids the use of sodium cyanide, the process is lengthy and requires protection and deprotection steps.

As shown in Scheme 3, CN 107501237 A and US 2018/201601 A1 disclose processes for the preparation of Apalutamide (1) which proceed through cyclobutanecarboxylic acid (D1) or an ester thereof (D2), respectively. In CN 107501237 A, Apalutamide (1) is produced by reaction of acid (D1) with pyridine (A) in the presence of thiophosgene, followed by treatment with refluxing methanolic hydrochloric acid. In US 2018/201601 A1, Apalutamide (1) is afforded by reaction of isothiocyanate (B) with the corresponding methyl ester (D2), derived from treatment of the acid (D1) with methyl iodide. These processes suffer from the use of harsh conditions, such as refluxing methanolic hydrochloric acid, or the use of hazardous alkylating agents, such as methyl iodide.

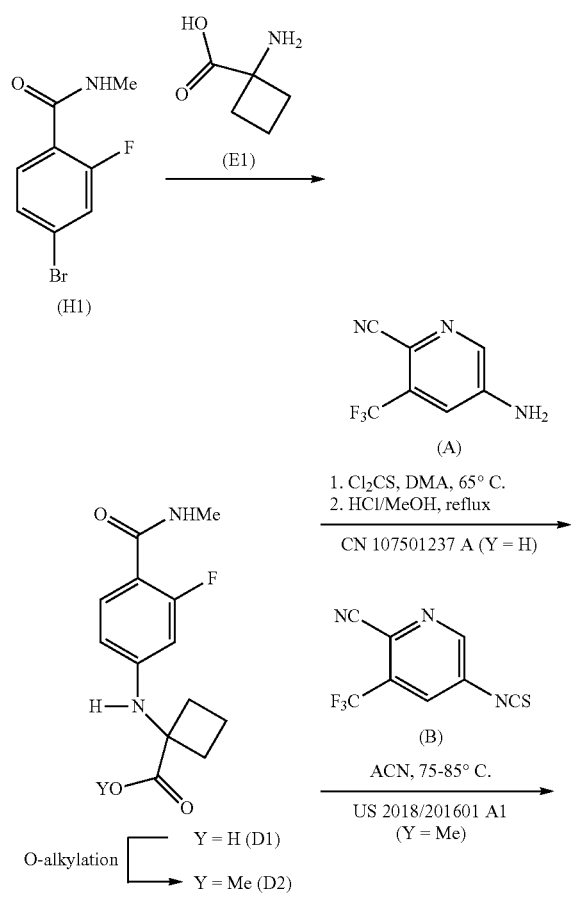

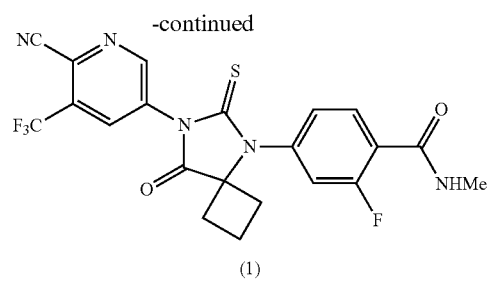

Owing to the drawbacks of the existing processes for the preparation of Apalutamide (1), there remains a need for improved processes for the preparation of Apalutamide (1), and the intermediates used in such preparations, that are more amenable to scale-up and use in a commercial setting.

SUMMARY

The present invention provides an improved process for the preparation of Apalutamide (1), as well as a new intermediate and processes for its preparation, as depicted in Scheme 4.

As shown in Scheme 4, in the processes of the present invention, Apalutamide (1) may be prepared by reaction of the isothiocyanate of Formula (7) with the intermediate of Formula (2), which can be prepared starting from either the compound of Formula (4) or the compound of Formula (6) upon reaction with cyclobutanecarboxylic acids of Formula (3) or Formula (5), respectively.

Scheme 4

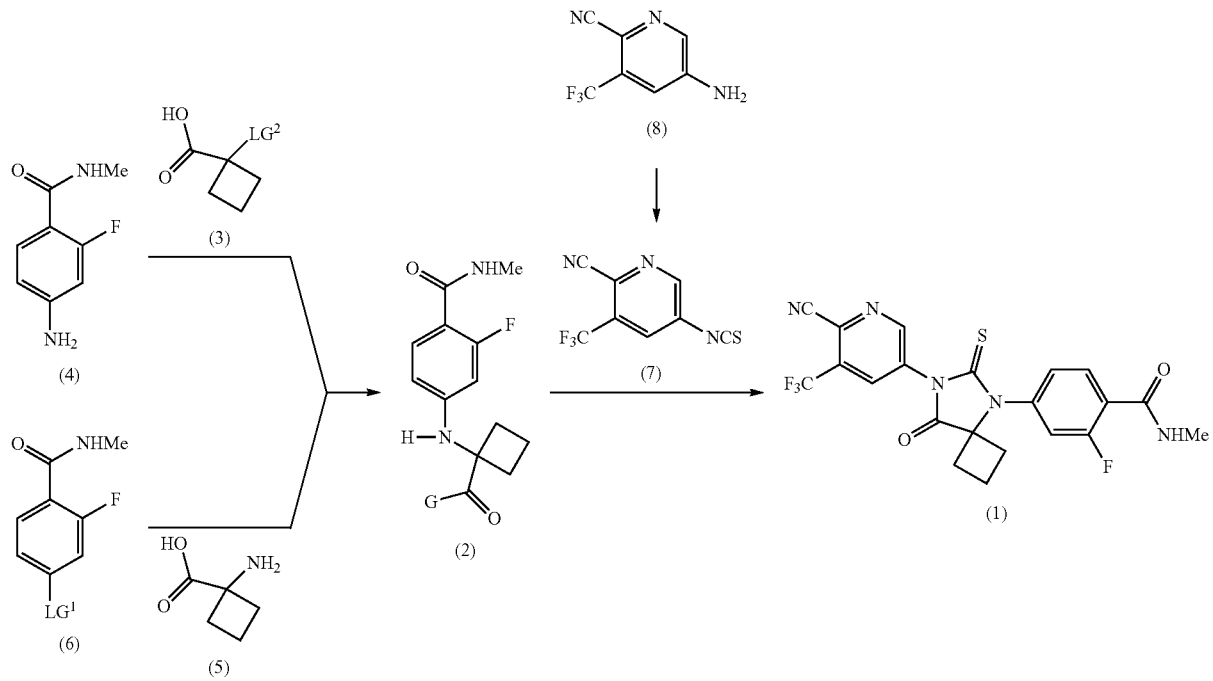

wherein

G is selected from the group consisting of OH and LG$^3$; and

LG$^1$, LG$^2$ and LG$^3$ are each independently a leaving group.

Thus, the process of the present invention provides a simplified method for the preparation of Apalutamide (1) that eliminates the need for protection and deprotection steps. Furthermore, the process of the present invention avoids the use of toxic and hazardous substances, such as cyanide salts and methyl iodide. Accordingly, the process of the present invention provides important advantages that are relevant to the commercial preparation of Apalutamide (1).

Accordingly, in a first aspect of the present invention, there is provided a process for preparing Apalutamide (1), comprising reaction, in the presence of a solvent (S5), of a compound of Formula (2), or a salt thereof, with the compound of Formula (7), wherein G in the compound of Formula (2) is selected from the group consisting of OH and LG$^3$; LG$^3$ is a leaving group selected from the group consisting of X and G$^1$; G$^1$ is selected from the group consisting of OR and A; X is halide; A is selected from the group consisting of:

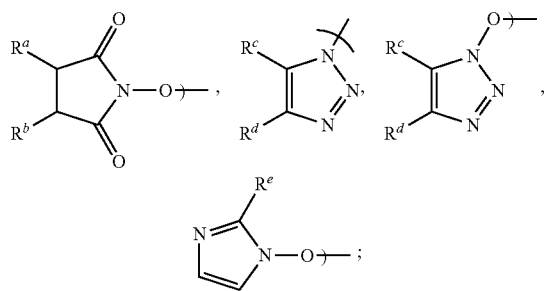

R is selected from the group consisting of a substituted or unsubstituted aliphatic group having 1 to 10 carbon atoms, a substituted or unsubstituted aryl group having 6 to 10 ring carbon atoms, and a substituted or unsubstituted arylalkyl group having 6 to 10 ring carbon atoms and 1 to 3 alkyl carbon atoms; R$^a$ and R$^b$ are either (a) hydrogen or (b) the groups R$^c$ and R$^d$; R$^c$ and R$^d$, taken together with the carbon atoms to which they are bonded form a ring selected from the group consisting of a substituted or unsubstituted aryl group having 6 to 10 ring carbon atoms, a substituted or unsubstituted heteroaryl group having 5 to 9 carbon atoms and at least one heteroatom selected from S, N and O, and a substituted or unsubstituted aliphatic group having 1 to 10 carbon atoms; and R$^e$ is hydrogen or methyl. Preferably, R is a substituted or unsubstituted aryl or arylalkyl group.

In a preferred embodiment of the first aspect, G is OH, and the compound of Formula (2) is the compound of Formula (2-A):

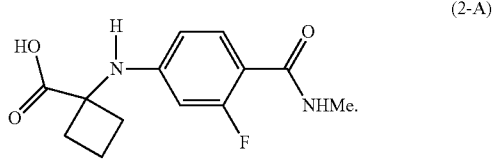 [SMILES: CNC(=O)c1ccc(NC2(C(=O)O)CCC2)cc1F]

(2-A)

In another preferred embodiment of the first aspect, G is LG$^3$, and the compound of Formula (2) is a compound of Formula (2-B):

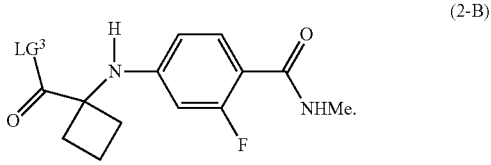 [SMILES: CNC(=O)c1ccc(NC2(C(=O)O)CCC2)cc1F]

(2-B)

Preferably, in the compound of Formula (2-B), $LG^3$ is $G^1$, and $G^1$ is OR, wherein R is selected from the group consisting of a substituted or unsubstituted aryl group having 6 to 10 ring carbon atoms, and a substituted or unsubstituted arylalkyl group having 6 to 10 ring carbon atoms and 1 to 3 alkyl carbon atoms.

In a further preferred embodiment of the first aspect, the solvent (S5) is selected from the group consisting of amides, dimethylsulfoxide and pyridine.

In a further preferred embodiment of the first aspect, the solvent (S5) is pyridine. In this preferred embodiment, G is preferably $LG^3$, $LG^3$ is $G^1$, and $G^1$ is OR, wherein R is selected from the group consisting of C1-C4 alkyl and substituted phenyl, wherein the phenyl substituent is selected from the group consisting of $NO_2$, chloride and fluoride. Most preferably, $G^1$ is methoxy.

In another preferred embodiment of the first aspect, the compound of Formula (2-B) is prepared by a process comprising displacement of the hydroxyl group of the carboxylic acid in the compound of Formula (2-A) with $LG^3$. In a further preferred embodiment, $LG^3$ is halide, and the displacement comprises reaction of the compound of Formula (2-A) with a halogenating agent selected from the group consisting of thionyl chloride, phosphorous trichloride and phosphorous pentachloride. Preferably, the halogenating agent is thionyl chloride.

Preferably, in the preparation of the compound of Formula (2-B), $LG^3$ is $G^1$, and the displacement comprises activation of the carboxylic acid group of the compound of Formula (2-A) by reaction with a carboxylic acid activating agent, followed by reaction of the resulting active acid derivative with a compound of Formula ($G^1$-H), wherein $G^1$ is selected from the group consisting of OR and A, wherein A is selected from the group consisting of:

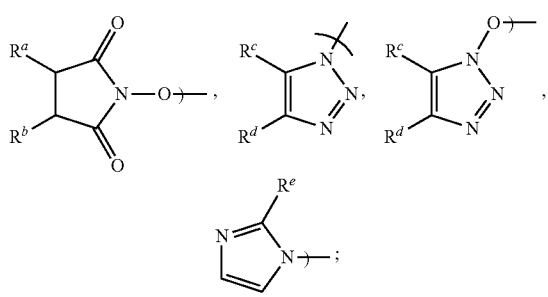

R is selected from the group consisting of a substituted or unsubstituted aliphatic group having 1 to 10 carbon atoms, a substituted or unsubstituted aryl group having 6 to 10 ring carbon atoms, and a substituted or unsubstituted arylalkyl group having 6 to 10 ring carbon atoms and 1 to 3 alkyl carbon atoms; $R^a$ and $R^b$ are either (a) hydrogen, or (b) the groups $R^c$ and $R^d$; $R^c$ and $R^d$, taken together with the carbon atoms to which they are bonded, form a ring selected from the group consisting of a substituted or unsubstituted aryl group having 6 to 10 ring carbon atoms, a substituted or unsubstituted heteroaryl group having 5 to 9 carbon atoms and at least one heteroatom selected from S, N and O, and a substituted or unsubstituted aliphatic group having 1 to 10 carbon atoms; and $R^e$ is hydrogen or methyl. Preferably, $G^1$ is OR.

In a further preferred embodiment for the preparation of the compound of Formula (2-B), the carboxylic acid activating agent is selected from the group consisting of thionyl chloride, pivaloyl chloride, N,N'-dicyclohexylcarbodiimide (DCC), N,N'-diisopropylcarbodiimide (DIC), N-(3-dimethylaminopropyl)-N'-ethylcarbodiimide (EDC) and N-(3-dimethylaminopropyl)-N'-ethylcarbodiimide hydrochloride (EDC.HCl). Preferably, the carboxylic acid activating agent is thionyl chloride, and $G^1$ is OR, wherein R is a C1-C4 alkyl group, and is most preferably methyl.

In another preferred embodiment of the first aspect, the compound of Formula (2-A) is prepared by a process comprising reaction, in the presence of a copper catalyst and a solvent (S1), of a compound of Formula (6) with the compound of Formula (5), or a salt thereof, wherein $LG^1$ in the compound of Formula (6) is a leaving group. Preferably, $LG^1$ is selected from the group consisting of halide, methanesulfonate, toluenesulfonate and trifluoromethanesulfonate, and, most preferably, $LG^1$ is bromide. Preferably, the copper catalyst is selected from the group consisting of Cu(0), Cu(I) and Cu(II) copper catalysts, and is most preferably, copper(I) iodide. In a further preferred embodiment, the reaction is conducted in the present of a ligand (L1). Preferably, ligand (L1) is a bidentate ligand selected from the group consisting of 2-acetylcyclohexanone, proline and ethylene glycol. In a further preferred embodiment, the reaction is conducted in the presence of a base (B1) selected from the group consisting of metal carbonates and metal bicarbonates.

In another preferred embodiment of the first aspect, the compound of Formula (2-A) is prepared by a process comprising reaction, in the presence of a solvent (S2), of the compound of Formula (4), or a salt thereof, with a compound of Formula (3), wherein $LG^2$ in the compound of Formula (3) is a leaving group. Preferably, $LG^2$ is selected from the group consisting of halide, methanesulfonate, toluenesulfonate and trifluoromethanesulfonate, and, most preferably, bromide. In a further preferred embodiment, the reaction is conducted in the presence of a base (B2) that is a tertiary amine.

In a second aspect of the present invention, there is provided a compound of Formula (2):

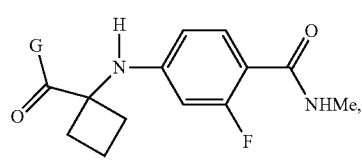

(2)

wherein G is $LG^3$; $LG^3$ is a leaving group selected from the group consisting of X and $G^1$; X is halide; $G^1$ is selected from the group consisting of OR and A; A is selected from the group consisting of:

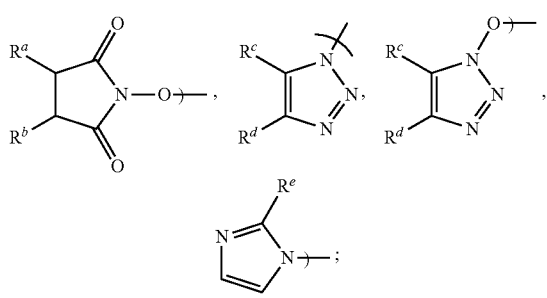

R is selected from the group consisting of a substituted or unsubstituted aliphatic group having 1 to 10 carbon atoms, a substituted or unsubstituted aryl group having 6 to 10 ring carbon atoms, and a substituted or unsubstituted arylalkyl group having 6 to 10 ring carbon atoms and 1 to 3 alkyl carbon atoms; $R^a$ and $R^b$ are either (a) hydrogen or (b) the groups $R^c$ and $R^d$; $R^c$ and $R^d$, taken together with the carbon atoms to which they are bonded form a ring selected from the group consisting of a substituted or unsubstituted aryl group having 6 to 10 ring carbon atoms, a substituted or unsubstituted heteroaryl group having 5 to 9 carbon atoms and at least one heteroatom selected from S, N and O, and a substituted or unsubstituted aliphatic group having 1 to 10 carbon atoms; and $R^e$ is hydrogen or methyl. Preferably, R is selected from the group consisting of a substituted or unsubstituted aryl group having 6 to 10 ring carbon atoms, and a substituted or unsubstituted arylalkyl group having 6 to 10 ring carbon atoms and 1 to 3 alkyl carbon atoms.

In preferred embodiments of the second aspect, $LG^3$ is $G^1$, and $G^1$ is OR or A. More preferably, $G^1$ is A, and most preferably, $G^1$ is an N-hydroxysuccinimide.

Other aspects and features of the present invention will become apparent to those ordinarily skilled in the art upon review of the following description of specific embodiments of the invention.

DETAILED DESCRIPTION

The processes of the present invention provide improvements in the preparation of Apalutamide (1) over known processes, including avoiding the use of protecting groups and the use of hazardous materials such as methyl iodide and cyanide salts, and are therefore more amenable to industrial application.

As used herein, the term "aliphatic", alone or as part of another substituent, means a straight chain, branched chain or non-aromatic cyclic hydrocarbon radical, or a combination thereof, which may be fully saturated, or mono- or polyunsaturated, and can include di- and multivalent radicals, having from 1 to 10 carbons. Preferably, an aliphatic group has from 1 to 5 carbons. Examples of saturated hydrocarbon radicals include, but are not limited to, groups such as methyl, ethyl, n-propyl, iso-propyl, n-butyl, t-butyl, iso-butyl, sec-butyl, hexanyl, 2-methyl-2-hexanyl, cyclohexyl, 1-methylcyclohexyl, cyclopropylmethyl, and isomers of, for example, n-pentyl, n-hexyl, n-heptyl and n-octyl. An unsaturated hydrocarbon radical is one having one or more double bonds or triple bonds. Examples of preferred unsaturated hydrocarbon radicals include vinyl, 2-propenyl, crotyl, 2-isopentenyl, 2-(butadienyl), 2,4-pentadienyl, 3-(1,4-pentadienyl), norbornenyl, ethynyl, 1-propynyl, 2-propynyl, and 3-butynyl.

As used herein, the term "alkyl", alone or as part of another substituent, means, unless otherwise stated, a straight or branched chain, saturated hydrocarbon radical having 1 to 4 carbon atoms. Examples of preferred alkyl groups include methyl, ethyl, n-propyl, iso-propyl, n-butyl, t-butyl, iso-butyl and sec-butyl. Particularly preferred alkyl groups include methyl, ethyl, n-propyl, iso-propyl, n-butyl, t-butyl, iso-butyl and sec-butyl.

As used herein, the term "aryl", alone or as part of another substituent, means a polyunsaturated, aromatic, hydrocarbon radical which can comprise one, two or three rings, which are fused together or linked covalently, having a total of 6 to 10 ring carbon atoms. Examples of preferred aryl groups include phenyl, 1-naphthyl and 2-naphthyl.

As used herein, the term "arylalkyl", alone or as part of another substituent, means an aryl substituent having 6 to 10 ring carbon atoms attached through an alkyl radical, having 1 to 3 carbon atoms, to the parent structure. Preferred examples of arylalkyl groups include benzyl and phenethyl.

As used herein, the term "substituted" refers to the replacement of one or more hydrogen atoms with a substituent selected from the group consisting of: alkyl, OR", halogen, CN, $NO_2$ and $CF_3$. A substituted group may be mono-substituted or poly-substituted. As used herein, each R" may be selected, independently, from the group consisting of hydrogen and alkyl groups. Preferred examples of substituent groups on substituted aliphatic, aryl and arylalkyl groups include $NO_2$, fluoride, chloride and trifluoromethyl.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

As used herein, the abbreviations DMF, DMSO and DMA refer to the solvents N, N-dimethylformamide, dimethyl sulfoxide and dimethylacetamide, respectively.

As used herein, the terms "wt %" or "% w/w" refer to weight percent and is used to express weight solute/weight solution as a percentage.

As used herein, the term "volumes" refers to the parts of solvent or liquids by volume (mL) with respect to the weight of solute (g). For example, when a reaction is conducted using 1 g of starting material and 100 mL of solvent, it is said that 100 volumes of solvent are used.

As used herein, "room temperature" generally refers to a temperature of 20-25° C.

As used herein, the term "about" means "close to", and that variation from the exact value that follows the term is within amounts that a person of skill in the art would understand to be reasonable. For example, when the term "about" is used with respect to temperature, a variation of ±5° C. is generally acceptable when carrying out the processes of the present invention; when used with respect to mole equivalents, a variation of ±0.1 moles is generally acceptable; and when used with respect to volumes, a variation of 10% is generally acceptable.

In one embodiment of the present invention, Apalutamide (1) and intermediates useful in the preparation thereof may be prepared by the processes as set out in Scheme 4. Exemplary reagents and conditions for these processes are described herein.

In the processes of the invention, Apalutamide (1) may be prepared from a compound of Formula (2). When G is OH, the compound of Formula (2) is a compound of Formula (2-A):

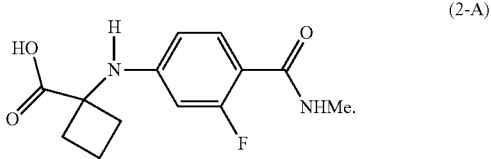

(2-A)

Preferably, in the processes of the invention, G is $LG^3$, and the compound of Formula (2) is a compound of Formula (2-B):

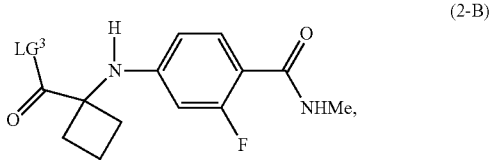 [SMILES: CNC(=O)c1ccc(NC2(C(=O)O)CCC2)cc1F]

(2-B)

wherein $LG^3$ is a leaving group. Preferably, $LG^3$ is selected from the group consisting of X and $G^1$, wherein:
  X is halide, and $G^1$ is selected from the group consisting of OR and A;
  A is selected from the group consisting of:

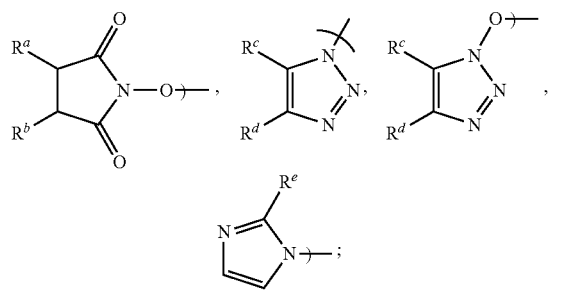

R is selected from the group consisting of a substituted or unsubstituted aliphatic group having 1 to 10 carbon atoms, a substituted or unsubstituted aryl group having 6 to 10 ring carbon atoms, and a substituted or unsubstituted arylalkyl group having 6 to 10 ring carbon atoms and 1 to 3 alkyl carbon atoms;
$R^a$ and $R^b$ are either (a) hydrogen, or (b) the groups $R^c$ and $R^d$;
$R^c$ and $R^d$, taken together with the carbon atoms to which they are bonded, form a ring selected from the group consisting of a substituted or unsubstituted aryl group having 6 to 10 ring carbon atoms, a substituted or unsubstituted heteroaryl group having 5 to 9 carbon atoms and at least one heteroatom selected from S, N and O, and a substituted or unsubstituted aliphatic group having 1 to 10 carbon atoms; and
$R^e$ is hydrogen or methyl.
Preferably, the halide X is chloride.
Preferably, when R is an aliphatic group, the aliphatic group is selected from the group consisting of methyl, ethyl, n-propyl, isopropyl, n-butyl, t-butyl, isobutyl, sec-butyl, hexanyl, 2-methyl-2-hexanyl, cyclohexyl, 1-methylcyclohexyl and cyclopropylmethyl. More preferably, the aliphatic group is C1-C2 alkyl, and most preferably, the aliphatic group is methyl. Substituted aliphatic groups are preferably substituted with methoxy.

Preferably, when R is an aryl group, the aryl group is selected from the group consisting of phenyl, 1-naphthyl, 2-naphthyl and 4-biphenyl, and is most preferably phenyl. Substituted aryl groups are preferably substituted with one or more substituents selected from the group consisting of halogen and $NO_2$, and most preferably chloride, fluoride or $NO_2$.

Preferably, when R is an arylalkyl group, the arylalkyl group is selected from the group consisting of benzyl and phenethyl. Substituted arylalkyl groups are preferably substituted with one or more substituents selected from the group consisting of R''', OR''', halogen and $NO_2$, wherein each R''' is methyl. Most preferably, the substituents are selected from halogen and $NO_2$.

Preferably, when $G^1$ is A: $R^a$ and $R^b$ are each hydrogen and A is N-hydroxysuccinimidyl; $R^c$ and $R^d$ taken together with the carbon atoms to which they are bonded form a phenyl ring and A is benzotriazolyl or N-hydroxybenzotriazolyl; or $R^e$ is hydrogen and the substituent A is imidazolyl. Most preferably, A is N-hydroxysuccinimidyl.

Most preferably, $LG^3$ is methoxy.

In another embodiment of the present invention, there is provided a process for the preparation of the compound of Formula (2-A):

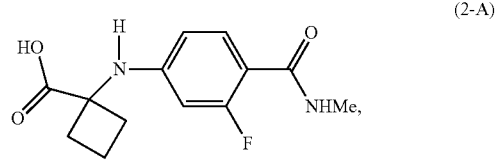

(2-A)

comprising reaction, in the presence of a copper catalyst and a solvent (S1), of a compound of Formula (6):

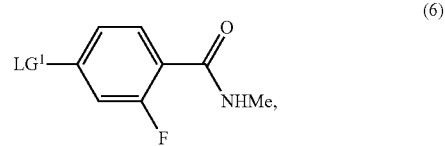

(6)

with the compound of Formula (5):

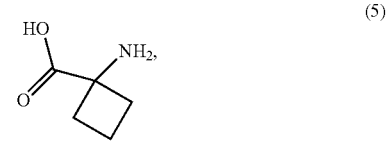

(5)

or a salt thereof,
wherein
  $LG^1$ is a leaving group.
In the compound of Formula (6), $LG^1$ is a leaving group selected from the group consisting of halides and sulfonates. Preferred sulfonates are selected from methanesulfonate, toluenesulfonate and trifluoromethanesulfonate. Preferably, LG$^1$ is halide selected from the group consisting of chloride, bromide and iodide, and is most preferably bromide.

The reaction of the compound of Formula (6) and the compound of Formula (5) is conducted in the presence of a copper catalyst selected from the group consisting of Cu(0), Cu(I) and Cu(II), preferably Cu(I) catalysts. Preferably, the Cu(I) catalyst is selected from the group consisting of copper(I) chloride, copper(I) bromide, copper(I) iodide, copper(I) oxide, copper(I) acetate, copper(I) thiocyanate and copper(I) sulfide, and is most preferably copper(I) iodide. Preferably, the Cu(II) catalyst is selected from the group consisting of copper(II) oxide, copper(II) chloride, copper(II) bromide, copper(II) sulfate, copper(II) acetate, copper(II) fluoride, copper(II) trifluoromethanesulfonate, copper(II) sulfide and copper(II) hydroxide, and is most preferably, copper(II) acetate. Preferably, the Cu(0) catalyst is selected from copper powder and copper sponge, and is most preferably copper sponge. Most preferably, the copper catalyst is copper(I) iodide. Preferably, the amount of copper catalyst relative to the compound of Formula (6) is between about 1 mol % and about 30 mol %, and is most preferably between about 10 mol % and about 25 mol %.

The reaction of the compound of Formula (6) and the compound of Formula (5) is preferably also conducted in the presence of a ligand (L1). Preferably, the ligand (L1) is a bidentate ligand selected from the group consisting of 2-acetylcyclohexanone, proline and ethylene glycol. Most preferably, the ligand (L1) is 2-acetylcyclohexanone. Preferably, the molar ratio of ligand (L1) relative to the copper catalyst is between about 1:1 to about 2:1, but most preferably about 1:1.

The reaction of the compound of Formula (6) and the compound of Formula (5) is preferably also conducted in the presence of base (B1), which can neutralise acid generated as a by-product during reaction, liberate the free form of the compound of Formula (5) when a salt is used and/or extract the acidic proton of the compound of Formula (5). Base (B1) is preferably selected from the group consisting of tertiary amines, metal carbonates and metal bicarbonates. Preferably, base (B1) is selected from the group consisting of sodium carbonate, sodium bicarbonate, potassium carbonate, potassium bicarbonate, lithium carbonate, triethylamine and diisopropylethylamine. Most preferably, base (B1) is selected from the group consisting of triethylamine, potassium carbonate and mixtures thereof.

The reaction of the compound of Formula (6) and the compound of Formula (5) is conducted in the presence of a solvent (S1). Solvent (S1) is preferably selected from the group consisting of water, halogenated hydrocarbons, amides, sulfoxides, aromatic hydrocarbons and miscible mixtures thereof. More preferably, solvent (S1) is selected from the group consisting of water, dichloromethane, N,N-dimethylformamide, N-methyl-2-pyrrolidone, dimethyl sulfoxide, toluene and miscible mixtures thereof. Most preferably, solvent (S1) is a mixture of N,N-dimethylformamide and water.

The reaction of the compound of Formula (6) and the compound of Formula (5) may be conducted at any suitable temperature, and is preferably conducted at a temperature between about room temperature and about 110° C., more preferably between about 80° C. and about 100° C.

In some cases, the compounds of Formula (5) and Formula (6) are commercially available compounds. Alternatively, the compounds of Formula (5) and Formula (6) may be prepared by any desired method including, for example, the methods described in Example 54 of WO 2006/021759 A1, WO 2005/019158 A1, and Chodnekar, M. S. et. al. *J. Med. Chem.* 1968, 11, 1023.

In another embodiment of the present invention, a process is provided for the preparation of the compound of Formula (2-A):

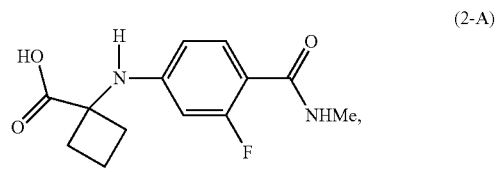 [SMILES: CNC(=O)c1ccc(NC2(C(=O)O)CCC2)cc1F]

(2-A)

comprising reaction, in the presence of a solvent (S2), of the compound of Formula (4):

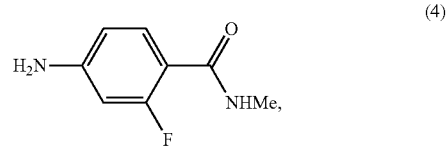 [SMILES: CNC(=O)c1ccc(N)cc1F]

(4)

or a salt thereof, with a compound of Formula (3):

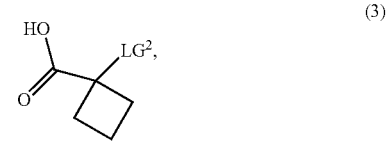

(3)

wherein
LG$^2$ is a leaving group.

In the compound of Formula (3), LG$^2$ is a leaving group selected from the group consisting of halides and sulfonates. Preferred sulfonates are selected from methanesulfonate, toluenesulfonate and trifluoromethanesulfonate. Preferably, LG$^2$ is halide selected from the group consisting of chloride, bromide and iodide, and is most preferably bromide.

The reaction of the compound of Formula (4) and the compound of Formula (3) is preferably conducted in the presence of base (B2), which can neutralise acid generated as a by-product during reaction, liberate the free form of the compound of Formula (4) when a salt is used, and/or extract the acidic proton of the compound of Formula (3). Base (B2) is preferably selected from the group consisting of tertiary amines, metal carbonates and metal bicarbonates, and more preferably, from tertiary amines. Preferably, base (B2) is selected from the group consisting of sodium carbonate, sodium bicarbonate, potassium carbonate, potassium bicarbonate, lithium carbonate, triethylamine and diisopropylethylamine. Most preferably, base (B2) is triethylamine, diisopropylethylamine or mixtures thereof.

The reaction of the compound of Formula (4) and the compound of Formula (3) is conducted in the presence of a solvent (S2). Solvent (S2) is preferably selected from the group consisting of halogenated hydrocarbons, ethers, nitriles and formamides. More preferably, solvent (S2) is selected from the group consisting of dichloromethane, tetrahydrofuran, methyl t-butyl ether, acetonitrile and N,N-dimethylformamide. Most preferably, solvent (S2) is dichloromethane.

The reaction of the compound of Formula (4) and the compound of Formula (3) may be conducted at any suitable temperature, and is preferably conducted at a temperature between about room temperature and the reflux temperature of the reaction mixture. Preferably, the reaction is conducted between about 35° C. and about 40° C.

The compounds of Formula (3) and Formula (4) are commercially available compounds. Alternatively, the compounds of Formula (3) and Formula (4) may be prepared by any desired method including, for example, the methods described in, Estieu et al. *Tet. Lett.* 1996, 37, 623, Example 30 of WO 2012/073138 A1 or Xu et al. *J. Chem. Res.* 2013, 37, 615.

In another embodiment of the present invention, there is provided a process for the preparation of the compound of Formula (2-B):

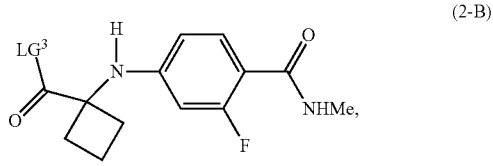

the process comprising displacement of the hydroxyl group in the carboxylic acid of the compound of Formula (2-A):

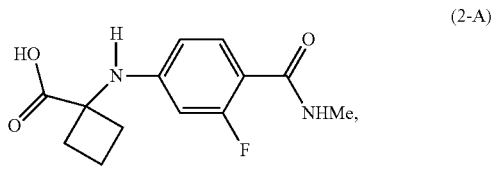 [SMILES: CNC(=O)c1ccc(NC2(C(=O)O)CCC2)cc1F]

with leaving group $LG^3$.

When $LG^3$ in the compound of Formula (2-B) is halide, the displacement comprises reaction of the compound of Formula (2-A) with a halogenating agent selected from the group consisting of thionyl chloride, phosphorous trichloride and phosphorous pentachloride. Preferably, the halogenating agent is thionyl chloride.

In the reaction of the compound of Formula (2-A) with a halogenating agent, the halogenating agent may also act as the solvent. Preferably, the reaction is conducted in the presence of a solvent (S3), which is preferably selected from the group consisting of halogenated hydrocarbons and aromatic hydrocarbons, and is most preferably dichloromethane or toluene.

The reaction of the compound of Formula (2-A) with a halogenating agent may be conducted at any suitable temperature, and is preferably conducted at a temperature between about room temperature and the reflux temperature of the reaction mixture. Preferably, the reaction is conducted between about 35° C. and about 40° C.

When $LG^3$ in the compound of Formula (2-B) is $G^1$, the displacement comprises activation of the carboxylic acid group of the compound of Formula (2-A) by reaction with a carboxylic acid activating agent followed by reaction of the activated acid derivative with a nucleophilic compound of Formula ($G^1$-H). The compound of Formula ($G^1$-H) is selected from the group consisting of an alcohol of Formula (ROH) and a compound of Formula (A-H), wherein (ROH) and (A-H) denote the saturated compound corresponding with the radical OR and A defined above.

In the activation of the carboxylic acid group of the compound of Formula (2-A), the carboxylic acid activating agent refers to an agent that enhances the reactivity of a free carboxylic acid group towards reaction with a nucleophile ($G^1$-H). Preferably, the carboxylic acid activating agent is an activating agent that reacts with the carboxylic acid of Formula (2-A) to form an active acid derivative. The active acid derivative is preferably selected from the group consisting of an acyl chloride, a mixed anhydride or a reactive ester, such as an O-acylisourea mixed anhydride. The carboxylic acid activating agent is preferably selected from the group consisting of thionyl chloride, pivaloyl chloride, N,N'-dicyclohexylcarbodiimide (DCC), N,N'-diisopropylcarbodiimide (DIC), N-(3-dimethylaminopropyl)-N'-ethylcarbodiimide (EDC), N-(3-dimethylaminopropyl)-N'-ethylcarbodiimide hydrochloride (EDC.HCl), and similar reagents. The carboxylic acid activating agent may also be a Lewis acid or a Brönsted acid, preferably selected from the group consisting of hydrogen chloride, sulfuric acid and p-toluenesulfonic acid. Most preferably, the carboxylic acid activating agent is thionyl chloride.

In the displacement of the hydroxyl of the carboxylic acid group when $LG^3$ is $G^1$, the carboxylic acid activating agent and/or the compound of Formula ($G^1$-H), may also act as solvent, when appropriate (if liquid). Alternatively, the reaction is conducted in the presence of a solvent (S4). Solvent (S4) is preferably selected from the group consisting of halogenated hydrocarbons, aromatic hydrocarbons, ethers, nitriles and formamides. Preferably, solvent (S4) is selected from the group consisting of dichloromethane, toluene, tetrahydrofuran, methyl t-butyl ether, acetonitrile and N,N-dimethylformamide. Most preferably, solvent (S4) is dichloromethane.

The displacement of the hydroxyl of the carboxylic acid group when $LG^3$ is $G^1$ is conducted at any suitable temperature, preferably at an elevated temperature, and more preferably, in the range of about 55° C. to about 75° C. Most preferably, the reaction temperature is in the range of about 60° C. to about 70° C.

The displacement of the hydroxyl of the carboxylic acid group when $LG^3$ is $G^1$ can be conducted in different modes depending on the nature of the carboxylic acid activating agent and the compound of Formula ($G^1$-H). In one embodiment, the displacement is conducted in a step-wise manner wherein the compound of Formula (2-A) is first treated with the carboxylic acid activating agent to form the active acid derivative before treatment of the reaction mixture with the compound of Formula ($G^1$-H). In other embodiments, the displacement is conducted in a 'one-pot' method wherein the carboxylic acid activating agent, the compound of Formula ($G^1$-H) and the compound of Formula (2-A) are combined to form a reaction mixture. The one-pot mode is preferred when the carboxylic acid activating agent is thionyl chloride or DCC.

In another embodiment of the present invention, there is provided a process for the preparation of Apalutamide (1):

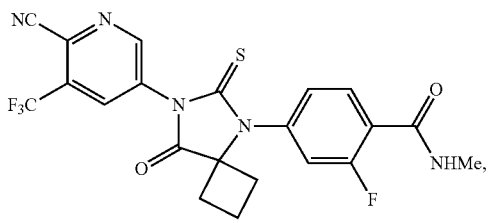
(1)

comprising coupling, in the presence of a solvent (S5) of a compound of Formula (2):

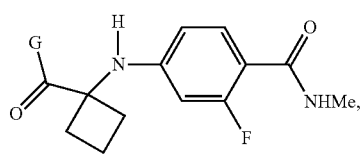
(2)

or a salt thereof, with the compound of Formula (7):

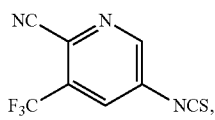
(7)

wherein

G is selected from the group consisting of OH and $LG^3$; and $LG^3$ is a leaving group.

The coupling of the compound of Formula (2) and the compound of Formula (7) is conducted in the presence of a solvent (S5). Solvent (S5) is preferably selected from the group consisting of amides, such as N,N-dimethylformamide, N,N-dimethylacetamide, formamide and N-methyl-2-pyrrolidone; carboxylic acids, such as acetic acid and formic acid; dimethylsulfoxide; and pyridine. Preferably, solvent (S5) is selected from the group consisting of N,N-dimethylformamide, N,N-dimethylacetamide, acetic acid, dimethylsulfoxide and pyridine. Most preferably, solvent (S5) is pyridine, which has been found to provide higher levels of conversion when compared to other solvents.

The coupling of the compound of Formula (2) and the compound of Formula (7) is conducted at any suitable temperature. Preferably, the temperature is in the range of room temperature to about 90° C. More preferably, the reaction temperature is in the range of about 40° C. to about 80° C.

In the coupling of the compound of Formula (2) and the compound of Formula (7), the molar ratio of the compound of Formula (7) to the compound of Formula (2) is preferably in the range of 1:1 to 3:1, and is preferably at least 2:1.

In another embodiment of the present invention, there is provided a compound of Formula (2):

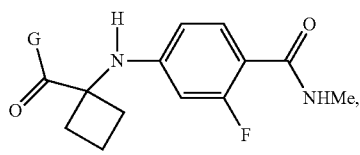
(2)

wherein
G is $LG^3$;
$LG^3$ is a leaving group selected from the group consisting of X and $G^1$;
X is halide; and
$G^1$ is selected from the group consisting of OR and A;
wherein
A is selected from the group consisting of:

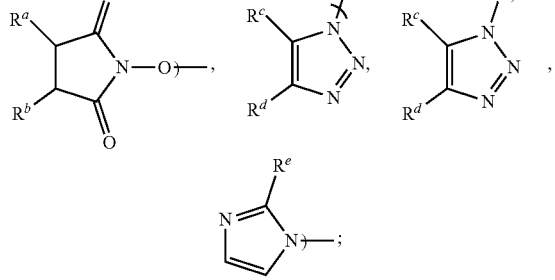

R is selected from the group consisting of a substituted or unsubstituted aryl group having 6 to 10 ring carbon atoms, and a substituted or unsubstituted arylalkyl group having 6 to 10 ring carbon atoms and 1 to 3 alkyl carbon atoms;

$R^a$ and $R^b$ are either (a) hydrogen or (b) the groups $R^c$ and $R^d$;

$R^c$ and $R^d$, taken together with the carbon atoms to which they are bonded, form a ring selected from the group consisting of a substituted or unsubstituted aryl group having 6 to 10 ring carbon atoms, a substituted or unsubstituted heteroaryl group having 5 to 9 carbon atoms and at least one heteroatom selected from S, N and O, and a substituted or unsubstituted aliphatic group having 1 to 10 carbon atoms; and $R^e$ is hydrogen or methyl.

EXAMPLES

The following examples are illustrative of some of the embodiments of the invention described herein. It will be apparent to the person skilled in the art that various alterations to the described processes in respect of the reactants, reagents and conditions may be made when using the processes of the present invention without departing from the scope or intent thereof.

Analysis Methods Used in the Exemplified Embodiments:

The method shown in Table 1 was used to determine the area % purity of the compound of Formula (2-A) and Formula (2-B1) as provided in Examples 3 and 4. This method was also used in the determination of the extent of reaction in the conversion of compounds of Formula (2-A), (2-B1) and (2-B2) to Apalutamide (1) as provided in Examples 6 to 9.

TABLE 1

HPLC method for the determination of purity and extent of reaction in exemplified embodiments

| | |
|---|---|
| Instrument | Waters 2695 HPLC |
| Column | Waters Symmetry C18, 4.6 × 150 mm, 3.5 μm |
| Column Temp. | 25° C. |
| Sample temp. | 20-25° C. |
| Mobile phase | Solution A: 0.5 mL formic acid in 1000 mL of nanopure water, filtered and degassed. |
| | Solution B: HPLC grade acetonitrile, filtered and degassed. |

| | Gradient | | |
|---|---|---|---|
| Mode | Time (min) | % Solution A | % Solution B |
| | 0.0 | 40 | 60 |
| | 10.00 | 30 | 70 |
| | 10.10 | 5 | 95 |
| | 13.00 | 5 | 95 |
| | 13.10 | 40 | 60 |
| | 18.0 | 40 | 60 |

| | |
|---|---|
| Flow rate | 0.8 mL/minute |
| Injection volume | 10 μL |
| Detector | 250 nm |
| Run time | 18 minutes |
| Sample prep. | Dissolved about 3-5 mg of sample in about 3 mL HPLC grade acetonitrile. |

The method shown in Table 2 was used to determine the extent of reaction of the compound of Formula (2-B3) to Apalutamide (1) as provided in Example 10.

TABLE 2

HPLC method for the determination of extent of reaction in exemplified embodiments

| | |
|---|---|
| Instrument | Waters 2695 HPLC |
| Column | Agilent Zorbax SB-CN, 5 μm, 4.6 × 250 mm |
| Column Temp. | 35° C. |
| Sample temp. | 20-25° C. |
| Mobile phase | Solution A: 0.5 mL formic acid in 1000 mL of nanopure water, filtered and degassed. |
| | Solution B: HPLC grade acetonitrile, filtered and degassed. |

| | Gradient | | |
|---|---|---|---|
| Mode | Time (min) | % Solution A | % Solution B |
| | 0.0 | 45 | 55 |
| | 10.00 | 35 | 65 |
| | 10.10 | 5 | 95 |
| | 13.00 | 5 | 95 |
| | 13.10 | 45 | 55 |
| | 18.0 | 45 | 55 |

| | |
|---|---|
| Flow rate | 1.0 mL/minute |
| Injection volume | 10 μL |
| Detector | 250 nm |
| Run time | 18 minutes |
| Sample prep. | Dissolved about 3-5 mg of sample in about 3 mL HPLC grade acetonitrile. |

Example 1: Preparation of 5-isothiocyanato-3-(trifluoromethyl)pyridine-2-carbonitrile (Compound of Formula (7))

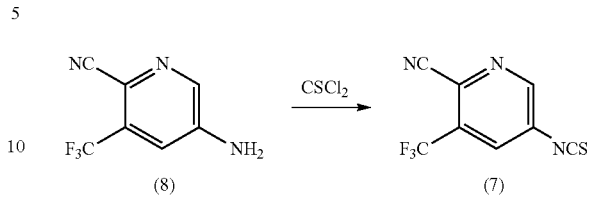

A biphasic mixture of the compound of Formula (8) (2.52 g, 13.47 mmol) in water (63 mL) and methylene chloride (25 mL) was treated with thiophosgene (2 mL, 26.09 mmol) dropwise at room temperature. The resulting mixture was allowed to stir at room temperature for 16 hours. After this time, additional methylene chloride (50 mL) was added to the clear, biphasic system, and the phases were separated. The aqueous layer was extracted with methylene chloride (50 mL), and the combined organic layers were washed with saturated sodium bicarbonate solution. Following separation, the organic layer was dried over sodium sulfate, filtered, concentrated and dried in vacuo at room temperature to afford the compound of Formula (7) (3.0 g, 97% yield) as an orange solid.

$^1$H-NMR of the compound of Formula (8): (CDCl$_3$, 300 MHz) δ: 7.86 (1H, d, J=2.2 Hz), 8.74 (1H, d, J=2.2 Hz).

Example 2: Preparation of 1-[3-fluoro-4-(methylcarbamoyl)anilino] cyclobutane-1-carboxylic acid (Compound of Formula (2-A))

To a slurry of the compound of Formula (6-A) (5.12 g, 22.06 mmol), the salt of Formula (5-S) (5.09 g, 33.58 mmol), copper(I) iodide (0.86 g, 4.52 mmol) and potassium carbonate (12.25 g, 88.63 mmol) in N,N-dimethylformamide (50 mL) was added water (5 mL), triethylamine (0.18 g, 1.78 mmol) and 2-acetylcyclohexanone (0.64 g, 4.57 mmol) at room temperature. The reaction mixture was heated to a temperature in the range of 95-100° C. and stirred for 60 hours, during which time the green slurry became purple. The reaction mixture was diluted with water (150 mL) and ethyl acetate (150 mL) and acidified to pH 4 with a solution of 1 M citric acid. Upon separation, the aqueous layer was further extracted with ethyl acetate (3×150 mL). The combined organic layers were then dried over sodium sulfate. Ethyl acetate was removed in vacuo and methylene chloride (400 mL) was added to the residue. The resulting slurry was cooled to 0-5° C., maintained at this temperature for 2 hours, and filtered. The filter cake was washed with methylene chloride (10 mL) and dried in vacuo at room temperature for 2 hours to afford the compound of Formula (2-A) (4.3 g, 76% yield) as a beige solid.

$^1$H-NMR of the compound of Formula (2-A): (DMSO-$d_6$, 300 MHz) δ: 1.83-2.07 (2H, m), 2.07-2.26 (2H, m), 2.53-2.68 (2H, m), 2.72 (3H, d, J=4.5 Hz), 6.00 (1H, dd, J=1.9, 14.3 Hz), 6.23 (1H, dd, J=2.0, 8.6 Hz), 7.17 (1H, s), 7.46 (1H, t, J=8.8 Hz), 7.57-7.75 (1H, m), 12.64 (1H, s).

Example 3: Preparation of 1-[3-fluoro-4-(methylcarbamoyl)anilino] cyclobutane-1-carboxylic acid (Compound of Formula (2-A))

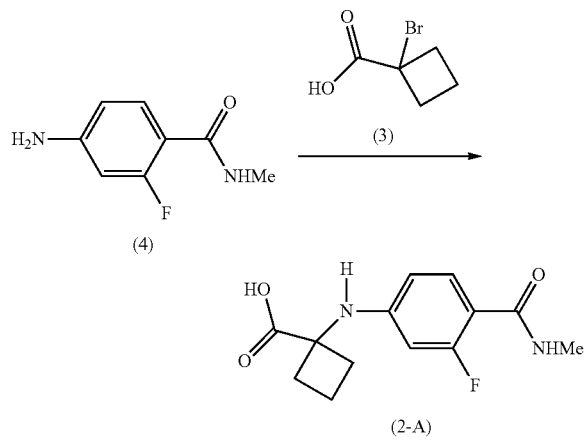

To a slurry of the compound of Formula (4) (5.03 g, 29.91 mmol) and the compound of Formula (3) (8.59 g, 47.99 mmol) in methylene chloride (50 mL) was added triethylamine (9.60 g, 94.87 mmol) dropwise at room temperature. The reaction mixture was allowed to stir at room temperature for 20 hours to afford a slurry. Diisopropylethylamine (7.90 g, 61.13 mmol) was then added and the mixture was heated to reflux, affording a clear solution. The reaction mixture was maintained at reflux for 4 days. Methylene chloride was removed in vacuo, and water (50 mL) was added to the residue, followed by concentrated hydrochloric acid (37 wt %; 3.8 mL). The resulting sludge-like material was stirred for 16 hours at room temperature, cooled to 2-5° C. for 4 hours, filtered and was washed with water (2×20 mL). The filter cake was dried in vacuo at room temperature for 16 hours to afford the compound of Formula (2-A) (7.3 g, 92% yield) as a beige solid.

A sample (2.3 g) of this material was subjected to further purification by treatment with saturated sodium bicarbonate solution (200 mL) and methylene chloride (200 mL). The resulting biphasic system was stirred at ambient temperature for 2 hours. Prior to separation of the layers, small amounts of insoluble solids were filtered and removed. The aqueous layer was acidified to a pH of less than 3 with concentrated hydrochloric acid (37 wt %), and the resulting slurry was stirred at ambient temperature for 2 hours, filtered and was washed with water (20 mL). The filter cake was dried in vacuo at room temperature for 15 hours, and then for 24 hours at 40° C., to afford the compound of Formula (2-A) (1.3 g, 58% yield from the 2.3 g crude sample) as a yellow solid. Chromatographic purity of the purified sample (HPLC, area %): 100.0%.

Example 4: Preparation of methyl 1-[3-fluoro-4-(methylcarbamoyl) anilino]cyclobutane-1-carboxylate (Compound of Formula (2-B1))

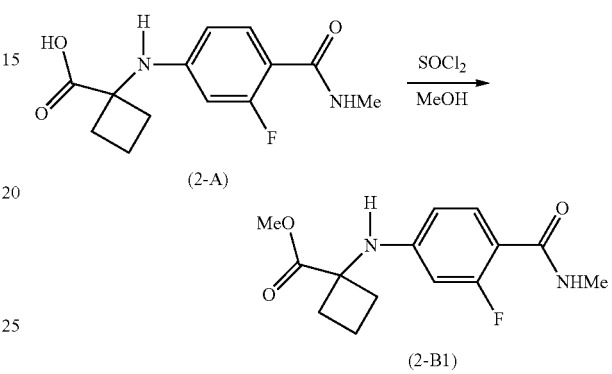

To a solution of the compound of Formula (2-A) (5.01 g, 18.82 mmol) in methanol (75 mL) was added thionyl chloride (3.20 g, 26.90 mmol) dropwise at 0-5° C. The reaction mixture was heated to 40° C. and maintained for 16 hours. Methanol and thionyl chloride were removed in vacuo, and methylene chloride (50 mL) and methyl t-butyl ether (50 mL) was added to the residue. The resulting slurry was stirred at room temperature for 1.5 hours, filtered, and the filter cake was washed with methyl t-butyl ether (20 mL). Methylene chloride and methyl t-butyl ether were removed from the filtrate in vacuo, and methyl t-butyl ether (100 mL) was added to the residue. The resulting slurry was stirred at ambient temperature for 1 hour, filtered, and was washed with methyl t-butyl ether (20 mL). The filter cake was dried in vacuo at room temperature for 1 hour to afford the compound of Formula (2-B1) (3.3 g, 63% yield) as a yellow solid. Chromatographic purity (HPLC, area %): 98.4%.

$^1$H-NMR of the compound of Formula (2-B1): (DMSO-$d_6$, 300 MHz) δ: 1.88-2.07 (2H, m), 2.08-2.26 (2H, m), 2.55-2.68 (2H, m), 2.72 (3H, d, J=4.4 Hz), 3.62 (3H, s), 5.99 (1H, dd, J=2.0, 14.2 Hz), 6.20 (1H, dd, J=2.1, 8.6 Hz), 7.27 (1H, broad s), 7.46 (1H, t, J=8.7 Hz), 7.57-7.75 (1H, m).

Example 5: Preparation of 1-[3-fluoro-4-methylcarbamoyl) anilino]cyclobutane-1-carbonyl chloride hydrochloride (Salt of Formula (2-B2S))

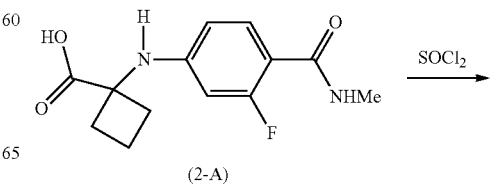

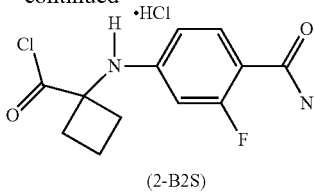

(2-B2S)

Thionyl chloride (1.00 g, 8.40 mmol) was added dropwise to a cooled (0-5° C.) slurry of the compound of Formula (2-A) (1.00 g, 3.76 mmol) in toluene (12 mL), and the reaction mixture was stirred at 60° C. for 1 hour, and then at 50° C. for 15 hours. The resulting slurry was filtered, and the filter cake was washed with toluene (20 mL). The filter cake was dried in vacuo at room temperature for 3 hours to afford crude salt of Formula (2-B2S) (1.08 g, 90% yield) as a dark solid. The solid was stirred in methylene chloride (20 mL) at room temperature for 1 hour, filtered and washed with methylene chloride (10 mL). The filter cake was then dried in vacuo at room temperature for a few minutes to afford the salt of Formula (2-B2S) (0.75 g, 70% yield) as a dark solid.

$^1$H-NMR of the compound of Formula (2-B2S): (DMSO-$d_6$, 300 MHz) δ: 1.85-2.06 (2H, m), 2.07-2.24 (2H, m), 2.53-2.66 (2H, m), 2.66-2.84 (4H, m), 6.01 (1H, dd, J=1.9, 14.3 Hz), 6.23 (1H, dd, J=2.0, 8.6 Hz), 7.46 (1H, t, J=8.7 Hz), 7.65 (2H, broad s).

Examples 6-10

Due to potent biological activity of Apalutamide (1), the Apalutamide (1) prepared in Examples 6-10 was not isolated. Yields and purities for these reactions were estimated by HPLC analysis of the products in solution.

Example 6: Preparation of Apalutamide (1) from the Compound of Formula (2-A)

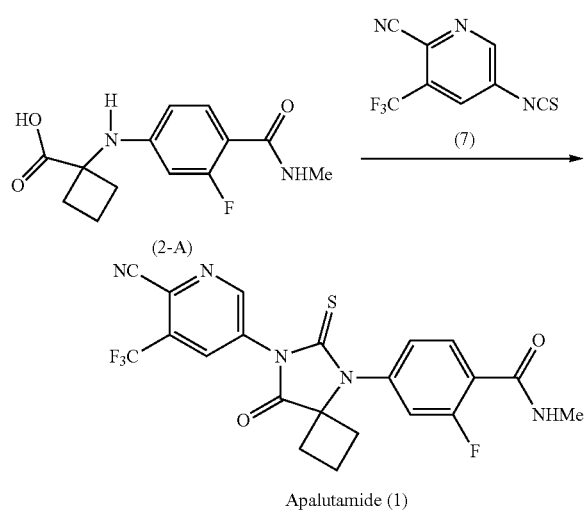

Apalutamide (1)

A small, sealed vial containing the compound of Formula (2-A) and the compound of Formula (7) in 0.6 mL of solvent (S5) was heated to 80° C. for 16 hours. The reaction mixture was analysed by HPLC and showed that all of the compound of Formula (2-A) was consumed. The reaction parameters are shown in Table 3.

TABLE 3

Reaction Parameters of Examples 6a-6c

| Example | Mass (mg) (2-A) | Mass (mg) (7) | Solvent (S5) | Time (h) |
|---|---|---|---|---|
| 6a | 29.1 | 61.5 | DMF | 16 |
| 6b | 28.4 | 63.9 | DMSO | 16 |
| 6c | 25.7 | 59.6 | Pyridine | 16 |

Example 7: Preparation of Apalutamide (1) from the Compound of Formula (2-B1)

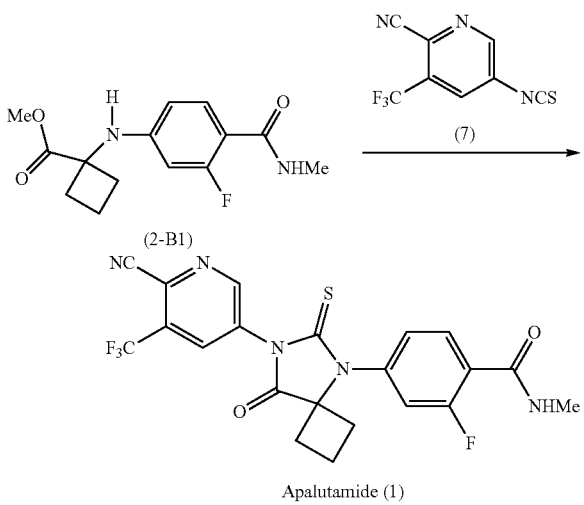

Apalutamide (1)

A small sealed vial containing the compound of Formula (2-B1) and the compound of Formula (7) in 0.6 mL of solvent (S5) was heated to 80° C. After 18 hours, the reaction mixture was analysed by HPLC and the area % ratio of Apalutamide (1):compound of Formula (2-B1) was determined. The reaction parameters and results of the HPLC analysis of the reaction mixtures are shown in Table 4.

TABLE 4

Reaction Parameters and HPLC Analysis of Examples 7a-7c

| Example | Mass (mg) (2-B1) | Mass (mg) (7) | Solvent (S5) | Time (h) | Area % (1):(2-B1) |
|---|---|---|---|---|---|
| 7a | 26.4 | 46.8 | DMA | 18 | 86:14 |
| 7b | 29.3 | 51.0 | DMSO | 18 | 89:11 |
| 7c | 27.7 | 58.2 | Pyridine | 18 | 95:5 |

LC-MS analysis of a control reaction performed in the absence of the compound of Formula (2-B1) showed that by-products and other impurities that were formed during the course of the reaction, which are not reported in Table 4, were related to side reactions of the compound of Formula (7), and not to consumption of the compound of Formula (2-B1). As such, the conversion shown in Table 4 is expected to reflect the yield of the reaction based on the limiting reagent of Formula (2-B1).

Example 8: Preparation of Apalutamide (1) from the Compound of Formula (2-B1)

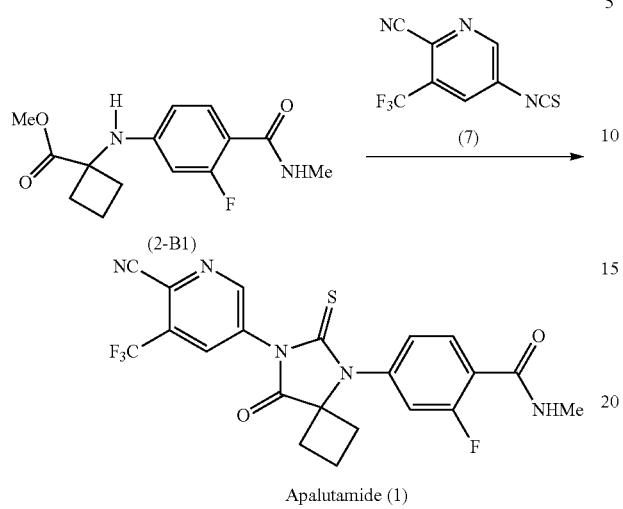

Apalutamide (1)

To a heated (60° C.) solution of the compound of Formula (2-B1) (27.6 mg, 0.098 mmol) in pyridine (0.15 mL) was added a solution of the compound of Formula (7) (77.4 mg, 0.338 mmol) in pyridine (0.5 mL) over 45 minutes. The reaction was allowed to stir at 60° C. for 2 hours, at which time HPLC analysis showed an area % ratio of Apalutamide (1):compound of Formula (2-B1) of 92:8. The reaction was allowed to stir at 60° C. for a further two hours at which time HPLC analysis showed an area % ratio of Apalutamide (1):compound of Formula (2-B1) of 95:5.

Example 9: Preparation of Apalutamide (1) from the Salt of Formula (2-62S)

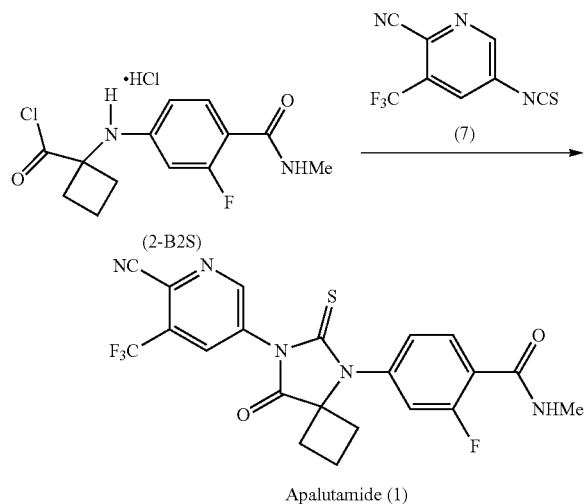

Apalutamide (1)

A small, sealed vial containing the salt of Formula (2-62S) (28.0 mg, 0.09834 mmol), the compound of Formula (7) (45.4 mg, 0.1981 mmol) and pyridine (1 mL) was allowed to stir at room temperature for 30 minutes. The reaction was then allowed to stir at 60° C. for 1 hour at which time HPLC analysis showed complete consumption of the compound of Formula (2-62S).

Example 10: Preparation of Apalutamide (1) from the Compound of Formula (2-B3)

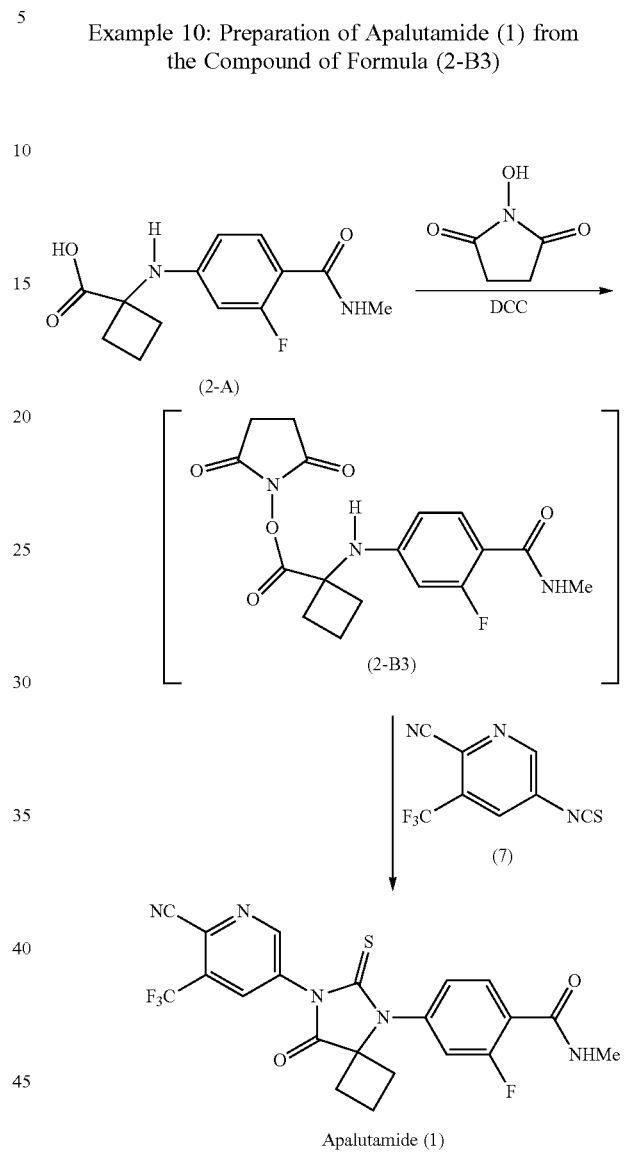

Apalutamide (1)

A cooled (−15 to −10° C.) solution of N,N'-dicyclohexylcarbodiimide (DCC) (190 mg, 0.921 mmol) in methylene chloride (1 mL) was added in ca. 10 portions over 20 minutes to a cold (−15 to −10° C.) slurry of the compound of Formula (2-A) (200 mg, 0.751 mmol) and N-hydroxysuccinimide (100 mg, 0.869 mmol) in methylene chloride (2 mL). The reaction mixture was warmed to −5 to 0° C., ethyl acetate (4 mL) was added, and stirring was maintained for 2 hours. The reaction mixture was then filtered, and the filtrate was concentrated in vacuo to afford 300 mg of the compound of Formula (2-B3). A small sealed vial containing a portion (28.8 mg) of the compound of Formula (2-B3), the compound of Formula (7) (35.3 mg, 0.154 mmol), and pyridine (1 mL) was allowed to stir at room temperature for 16 hours, and then heated to 60° C. for 4 days, at which time HPLC analysis showed an area % ratio of 87:13 for Apalutamide (1):the compound of Formula (2-A).

What is claimed is:
1. A process for the preparation of Apalutamide (1):

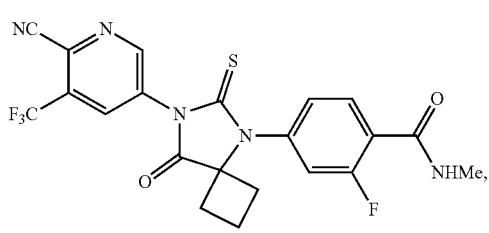

comprising reaction, in the presence of a solvent (S5), of a compound of Formula (2):

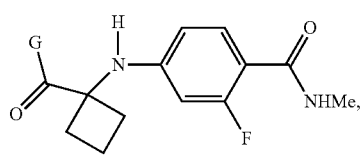

or a salt thereof, with the compound of Formula (7):

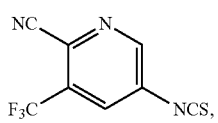

wherein
G is selected from the group consisting of OH and $LG^3$;
$LG^3$ is a leaving group selected from the group consisting of X and $G^1$;
$G^1$ is selected from the group consisting of OR and A;
X is halide;
A is selected from the group consisting of:

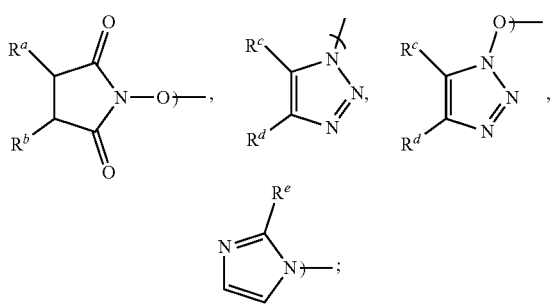

R is selected from the group consisting of a substituted or unsubstituted aliphatic group having 1 to 10 carbon atoms, a substituted or unsubstituted aryl group having 6 to 10 ring carbon atoms, and a substituted or unsubstituted arylalkyl group having 6 to 10 ring carbon atoms and 1 to 3 alkyl carbon atoms;
$R^a$ and $R^b$ are either (a) hydrogen, or (b) the groups $R^c$ and $R^d$;

$R^c$ and $R^d$, taken together with the carbon atoms to which they are bonded form a ring selected from the group consisting of a substituted or unsubstituted aryl group having 6 to 10 ring carbon atoms, a substituted or unsubstituted heteroaryl group having 5 to 9 carbon atoms and at least one heteroatom selected from S, N and O, and a substituted or unsubstituted aliphatic group having 1 to 10 carbon atoms; and
$R^e$ is hydrogen or methyl.

2. The process of claim 1, wherein G is $LG^3$, and the compound of Formula (2) is the compound of Formula (2-B):

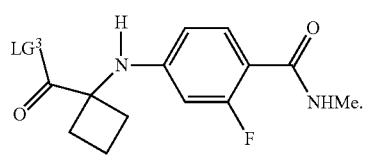

3. The process of claim 2, wherein R is selected from the group consisting of a substituted or unsubstituted aryl group having 6 to 10 ring carbon atoms, and a substituted or unsubstituted arylalkyl group having 6 to 10 ring carbon atoms and 1 to 3 alkyl carbon atoms.

4. The process of claim 3, wherein the solvent (S5) is selected from the group consisting of amides, dimethylsulfoxide and pyridine.

5. The process of claim 1, wherein the solvent (S5) is pyridine.

6. The process of claim 5, wherein G is OR and R is selected from the group consisting of C1-C4 alkyl and substituted phenyl, wherein the phenyl substituent is selected from the group consisting of $NO_2$, chloride and fluoride.

7. The process of claim 6, wherein G is methoxy.

8. The process of claim 2, wherein the compound of Formula (2-B) is prepared by a process comprising displacement of the hydroxyl group of the carboxylic acid in a compound of Formula (2-A):

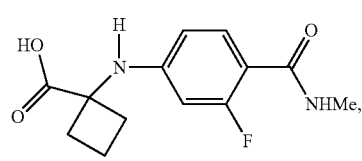

with $LG^3$.

9. The process of claim 8, wherein $LG^3$ is halide, and the displacement comprises reaction of the compound of Formula (2-A) with a halogenating agent selected from the group consisting of thionyl chloride, phosphorous trichloride and phosphorous pentachloride.

10. The process of claim 9, wherein the halogenating agent is thionyl chloride.

11. The process of claim 8, wherein $LG^3$ is $G^1$ and the displacement comprises activation of the carboxylic acid group of the compound of Formula (2-A) by reaction with a carboxylic acid activating agent, followed by reaction of the resulting active acid derivative with a compound of Formula ($G^1$-H), wherein $G^1$ is selected from the group consisting of OR and A, wherein
A is selected from the group consisting of:

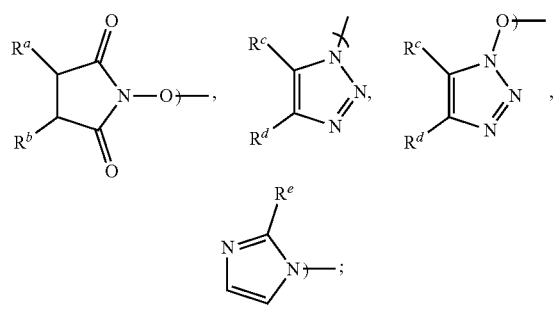

R is selected from the group consisting of a substituted or unsubstituted aliphatic group having 1 to 10 carbon atoms, a substituted or unsubstituted aryl group having 6 to 10 ring carbon atoms, and a substituted or unsubstituted arylalkyl group having 6 to 10 ring carbon atoms and 1 to 3 alkyl carbon atoms;

$R^a$ and $R^b$ are either (a) hydrogen, or (b) the groups $R^c$ and $R^d$;

$R^c$ and $R^d$, taken together with the carbon atoms to which they are bonded, form a ring selected from the group consisting of a substituted or unsubstituted aryl group having 6 to 10 ring carbon atoms, a substituted or unsubstituted heteroaryl group having 5 to 9 carbon atoms and at least one heteroatom selected from S, N and O, and a substituted or unsubstituted aliphatic group having 1 to 10 carbon atoms; and $R^e$ is hydrogen or methyl.

12. The process of claim 11, wherein $G^1$ is OR.

13. The process of claim 12, wherein the carboxylic acid activating agent is selected from the group consisting of thionyl chloride, pivaloyl chloride, N,N'-dicyclohexylcarbodiimide (DCC), N,N'-diisopropylcarbodiimide (DIC), N-(3-dimethylaminopropyl)-N'-ethylcarbodiimide (EDC) and N-(3-dimethylaminopropyl)-N'-ethylcarbodiimide hydrochloride (EDC.HCl).

14. The process of claim 13, wherein the carboxylic acid activating agent is thionyl chloride and R is a C1-C4 alkyl group.

15. The process of claim 14, wherein R is methyl.

16. The process of claim 8, wherein the compound of Formula (2-A) is prepared by a process comprising reaction, in the presence of a copper catalyst and a solvent (S1), of a compound of Formula (6):

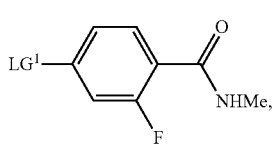

with the compound of Formula (5):

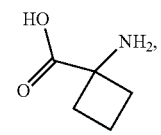

or a salt thereof,
wherein
$LG^1$ is a leaving group.

17. The process of claim 16, wherein $LG^1$ is bromide.

18. The process of claim 17, wherein the copper catalyst is copper(I) iodide.

19. The process of claim 18, wherein the reaction is conducted in the presence of a ligand (L1) selected from the group consisting of 2-acetylcyclohexanone, proline and ethylene glycol.

* * * * *